United States Patent
Auvray et al.

(10) Patent No.: US 11,559,274 B2
(45) Date of Patent: Jan. 24, 2023

(54) CONTRAST INJECTION IMAGING

(71) Applicant: KONINKLIJKE PHILIPS N.V., Eindhoven (NL)

(72) Inventors: Vincent Maurice Andre Auvray, Meudon (FR); Pierre Henri Lelong, Saint-Mande (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 258 days.

(21) Appl. No.: 16/495,627

(22) PCT Filed: Mar. 2, 2018

(86) PCT No.: PCT/EP2018/055194
§ 371 (c)(1),
(2) Date: Sep. 19, 2019

(87) PCT Pub. No.: WO2018/172040
PCT Pub. Date: Sep. 27, 2018

(65) Prior Publication Data
US 2020/0046309 A1    Feb. 13, 2020

(30) Foreign Application Priority Data
Mar. 20, 2017  (EP) ..................... 17305303

(51) Int. Cl.
*A61B 6/00*   (2006.01)
*A61B 6/12*   (2006.01)
(Continued)

(52) U.S. Cl.
CPC ............ *A61B 6/5288* (2013.01); *A61B 5/318* (2021.01); *A61B 6/12* (2013.01); *A61B 6/463* (2013.01);
(Continued)

(58) Field of Classification Search
CPC ......... A61B 6/5288; A61B 6/12; A61B 6/463; A61B 6/481; A61B 6/487; A61B 6/504;
(Continued)

(56) References Cited

U.S. PATENT DOCUMENTS 4,006,736 A * 2/1977 Kranys ............. A61M 5/14546
                                                600/432
4,878,115 A   10/1989 Elion
(Continued)

FOREIGN PATENT DOCUMENTS

DE      4133018 A1    4/1993
WO   2005020147 A1    3/2005
(Continued)

OTHER PUBLICATIONS

Dictionary definition of "puff" (www.dictionary.com/browse/puff, retrieved Nov. 26, 2021).*
(Continued)

*Primary Examiner* — Carolyn A Pehlke (57) ABSTRACT

Imaging systems and methods for imaging assisted interventional procedure that receive images of a region of interest, that automatically detect in the images a contrast agent puff as it courses through the region of interest, and that generate a display including a video replay loop of contrast enhanced images based on the automatic detection of the contrast agent puff.

19 Claims, 3 Drawing Sheets

(51) Int. Cl.
    *G06T 7/00*      (2017.01)
    *A61B 5/318*     (2021.01)
(52) U.S. Cl.
    CPC .............. *A61B 6/481* (2013.01); *A61B 6/487* (2013.01); *G06T 7/0012* (2013.01); *G06T 2207/30101* (2013.01)
(58) Field of Classification Search
    CPC ........ G06T 7/0012; G06T 2207/30101; A61M 5/007
    See application file for complete search history.

(56)         References Cited

U.S. PATENT DOCUMENTS

| 5,851,184 A * | 12/1998 | Goethel | A61B 6/481 |
| | | | 600/431 |
| 9,292,921 B2 | 3/2016 | Chen et al. | |
| 9,545,237 B2 | 1/2017 | Florent | |
| 2003/0018252 A1 | 1/2003 | Duchon | |
| 2008/0221439 A1 | 9/2008 | Iddan | |
| 2010/0063389 A1* | 3/2010 | Florent | A61B 6/12 |
| | | | 600/431 |
| 2010/0161023 A1* | 6/2010 | Cohen | A61B 17/1204 |
| | | | 623/1.11 |
| 2010/0208973 A1 | 8/2010 | Lienard et al. | |
| 2012/0230558 A1 | 9/2012 | Chen et al. | |
| 2014/0039303 A1* | 2/2014 | Kanzaki | A61B 6/504 |
| | | | 600/424 |
| 2014/0371578 A1* | 12/2014 | Auvray | A61B 6/503 |
| | | | 600/424 |
| 2015/0179148 A1 | 6/2015 | Auvray et al. | |

FOREIGN PATENT DOCUMENTS

WO       2006103644 A1    10/2006
WO    WO-2008107905 A2 *  9/2008    ............ A61M 5/007

OTHER PUBLICATIONS

Jin, Zhi-geng, et al. "Correlation between dual-axis rotational coronary angiography and intravascular ultrasound in a coronary lesion assessment." The international journal of cardiovascular imaging 33.2 (2017): 153-160.*

PCT/EP2018/055194, ISR & WO, May 4, 2018, 14 Page Document.

* cited by examiner

CONTRAST INJECTION IMAGING

CROSS-REFERENCE TO PRIOR APPLICATIONS

This application is the U.S. National Phase application under 35 U.S.C. § 371 of International Application No. PCT/EP2018/055194, filed on Mar. 2, 2018, which claims the benefit of European Patent Application No. 17305303.4, filed on Mar. 20, 2017. These applications are hereby incorporated by reference herein.

FIELD OF THE INVENTION

The technical field generally relates to contrast enhanced imaging of a patient's vasculature. In particular, the technical field relates to imaging contrast agent injections during interventional procedures.

BACKGROUND OF THE INVENTION

U.S. Pat. No. 9,545,237 discloses a system for recording and displaying a geometry of a vessel or generally a vascular structure, in which an injection catheter is inserted. A guide-wire tip is conducted by a guide-wire in order to examine and treat a stenosis at a coronary artery. A location of the guide-wire tip may be detected by means of X-ray, but it is difficult to illustrate the stenosis, since the coronary artery generally is invisible with respect to X-ray radiation. Therefore, a contrast agent may be provided via the injection catheter in order to increase the contrast of the vascular structure, in particular the coronary artery including the stenosis.

In a diagnosis or examination phase, a clinician injects a large dose of contrast agent and an angiography examination is performed. The clinician steers a guide wire, for example, based on the high quality angiography acquired during the diagnosis or examination phase. However, in difficult cases (such as passing a complex stenosis, going in a particular branch at a complex bifurcation), the clinician may need a more recent view of the vessels to observe exactly where the guide wire is with respect to the stenosis/bifurcation. In those cases, the clinician injects puffs (low dose, transient contrast agent injections).

A clinician typically injects the contrast agent as a short puff of contrast agent during a fluoroscopic, or other imaging modality, examination. The contrast agent injection results in short waves of contrast enhanced imaging that accurately, but briefly, delineate current vessels of interest.

Such transient contrast puffs course over the image in less than 1 second in some cases. It is difficult for the clinician to fully take in, and keep in mind, information presented by imaging the contrast puff when the display occurs over such a short period of time. Repeat puff injections may, therefore, be required for a second look at the vessel region of interest. Such repeat puff injections are inconvenient for the clinician and each comes with a frustration of having to view the information so briefly. Further, use of contrast agent should be minimized for reasons of patient health.

Thus, it is desired to provide an imaging and display technique that allows vessel structures in a region of interest to be effectively visualized by a clinician during an imaging assisted interventional procedure, despite a transient nature of the contrast agent injection. It is further desirable to provide a visualization technique that allows a clinician to reduce a number of contrast agent injections, or puffs, during the procedure.

SUMMARY OF THE INVENTION

Hence, there may be a need to provide an improved and facilitated way of generating imaging displays of an imaging assisted interventional procedure.

Generally, the present invention proposes to provide imaging systems and methods that receive images a region of interest, that automatically detect in the images a contrast agent puff as it courses through the region of interest, and that generate a display including a replay loop of contrast enhanced images based on the automatic detection of the contrast agent puff. Such a looped presentation of images allows a clinician to analyze vasculature details repeatedly and in depth, thereby ensuring that relevant information for accurate interventional procedures is persistently available to the clinician for reference. Since a video, in the form of a loop of contrast enhanced images, can be played in combination with live fluoroscopy, it can serve as an up-to-date local roadmap for the clinician's next steps in the procedure. Additionally, other details of the neighboring vasculature are displayed to the clinician, limiting a number of additional puffs required. That is, another part of the vasculature may be made visible, that is not of immediate interest to the clinician. However, it remains visible in the playback loop allowing the clinician to see how the vasculature looks like more distally without having to perform another contrast agent injection.

The object of the present invention is solved by the subject-matter of the independent claims; wherein further embodiments are incorporated in the dependent claims. It should be noted that the following described aspects of the invention apply also for the image processing system, for the imaging system, for the medical system and for the computer implemented method as well as for the computer program element and the computer readable medium.

Computer implemented methods for imaging, imaging systems and computer programs are provided for imaging. Features of the imaging systems, methods for imaging and computer programs are described in the following.

In one embodiment, an imaging system is provided. The imaging system includes a data receiver configured to receive a stream of images, a contrast agent detector, an image extractor and a display generator. The contrast agent detector and the image extractor are configured to identify images that have been contrast enhanced and to extract the identified images from the stream of images. The display generator is configured to generate a display including live images from the stream of images and a playback loop of the exacted images.

The live images allow progress of an interventional tool to be monitored by a clinician. The live images may be x-ray images that are not contrast enhanced and thus do not show vessels in the region of interest. The playback loop of extracted images allows a transient contrast injection to be viewed simultaneously by the clinician to garner information on the vessels being traversed by the interventional tool. The playback loop allows the contrast enhanced images to be repeatedly displayed after the contrast agent has dispersed in the body, thereby providing relevant information to the clinician in a more effective way and making it possible to reduce an overall number or amount of contrast agent injections.

In embodiments, the contrast agent detector is configured to automatically detect images that have been contrast enhanced through an image processing technique that filters contrast enhanced images from images that have not been contrast enhanced. For example, the image processing technique is configured to monitor a contrast indicating parameter and to determine an increase in the contrast indicating parameter as compared to the typical variations of the contrast indicating parameter over non-injected images. Thus, the contrast agent detector and the image extractor are configured to extract a temporal cluster of images that have been contrast enhanced from the stream of images that include images that have not been contrast enhanced. In this way, only relevant images related to the contrast puff are presented to the clinician in the playback loop.

In embodiments, the image extractor is configured to change a temporal length of the identified images for temporal cardiac cycle fitting. In embodiments, the image extractor is configured to trim or extend the identified images to temporally fit with one cardiac cycle or an integer number of cardiac cycles. That is, the contrast agent detector and the image extractor are configured to identify a set of images that have been contrast enhanced and to extract the identified images from the stream of images. The set of images are trimmed or extended in temporal length. The processes of changing the temporal length of the identified images/trimming or extending the identified images can be performed by adding or removing images (e.g. frames). By executing temporal cardiac cycle fitting on the length of the identified images, a smooth looped playback video is observed by the clinician.

In embodiments, a cardiac synchronizer is configured to temporally synchronize the extracted images and the live images with respect to cardiac phases. In this way, any movement in the live images due to the heart beating will be synchronized with corresponding movement due to the heart beating in the playback loop, thereby providing a presentation of the images that is intuitive to understand for the clinician. In embodiments, the display generator is configured to generate the display including the live images and the playback loop of the extracted images that are temporally synchronized to one another with respect to cardiac phases. In embodiments, the cardiac synchronizer uses identified images that have been changed in temporal length to fit with a cardiac cycle by the image extractor as has been described above.

In embodiments, a cardiac signal generator is configured to output a cardiac signal for use in cardiac synchronization and temporal cardiac cycle fitting. The cardiac signal is indicative of a cardiac cycle. The cardiac signal generator includes at least one of an electrocardiogram sensor and an image processing technique configured to derive the cardiac signal from the images.

In embodiments, a localizer is configured to operate with the contrast agent detector and the image extractor to identify images that have been contrast enhanced in a localized area of a more global field of view of the stream of images and to extract the identified images having the contrasted enhanced localized area from the stream of images. In this way, a local of area of interest can form the focus of the generated playback loop, thereby ensuring relevance of the images that have been detected, extracted and formed into a looping video. Generally, the clinician is interested in the vasculature close to an interventional tool. Information on what vessels look like in a different branch are of limited relevance. Accordingly, the localizer allows optimal relevance and focusing of the looping video.

In embodiments the localizer is configured to determine the localized area based on identification of an object of interest through an image processing technique. The object of interest can be a stent, a stenosis of a vessel or a tip of an interventional tool.

In embodiments, a gated contrast injection controller is configured to generate a contrast injection control that is at least one heart cycle in length. The gated contrast injection controller may be in communication with the cardiac signal generator. In this way, a sufficiently long contrast injection is ensured, which assists in generating a smooth playback video.

In embodiments, the identified images have been contrast enhanced through a puff injection of contrast agent. A puff injection may last 1 second or less from the start to the end of contrast injection, half a second or less or a quarter of a second or less.

In embodiments, the imaging system comprises an image acquisition machine for generating the stream of images.

In embodiments, the imaging system comprises a display device for displaying the playback loop.

In embodiments, the imaging system comprises an interventional tool that is imaged in the live imaging.

In embodiments, the imaging system comprises an electrocardiogram sensor for performing cardiac synchronization and cardiac cycle fitting as described herein.

Also disclosed is a computer program element adapted to implement an imaging system as described herein or adapted to perform the method steps described herein when executed by at least one processor.

A computer readable medium is also provided having stored thereon, the computer program element.

These and other aspects of the invention will be apparent from and elucidated with reference to the embodiment(s) described hereinafter.

SHORT DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

The following detailed description is merely exemplary in nature and is not intended to limit the application and uses. Furthermore, there is no intention to be bound by any expressed or implied theory presented in the preceding technical field, background, brief summary or the following detailed description.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

Figure 1:
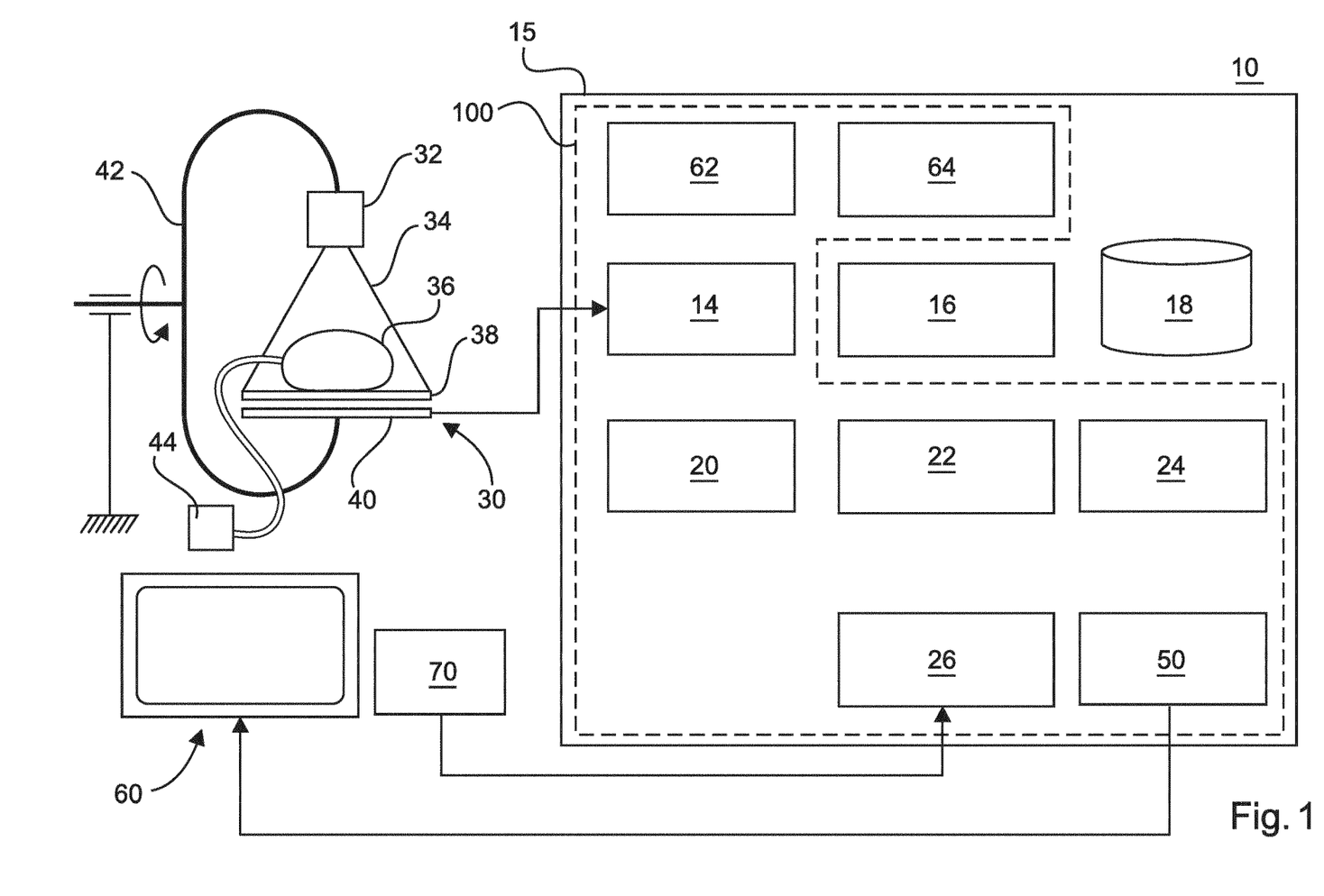
FIG. 1 is a schematic view of an imaging system including a controller, a display device, an electrocardiogram sensor and an image acquisition machine, in accordance with various embodiments.

FIG. 1 is a schematic view of an imaging system 10 including a controller 15, a display device 60, an electrocardiogram sensor 70 and an image acquisition machine 30, in accordance with various embodiments. The imaging system 10 is configured to display live images of an interventional tool 44 within a patient 36 during an interventional procedure and a video playback loop of images that include a contrast enhanced phase of the interventional procedure.

The image acquisition machine 30 is configured for generating a stream of images of a patient 36 supported on a table 38. In the illustrated embodiment, the image acquisition machine 30 includes a detector 40 and a source 32. The image acquisition machine 30 is configured for X-ray imaging, in accordance with various embodiments. The image acquisition machine 30 is, in embodiments, configured for angiographic image acquisition. In a specific embodiment, the imaging acquisition machine 30 has a C-arm 42 configuration, with the detector 14 at one end of the C-arm 42 and the source 32 at the other end of the C-arm 42. The image acquisition machine 30 is configured to obtain fluoroscopic images of a vessel region of interest of the patient 36 including the interventional tool 44 in situ, in accordance with various embodiments. The obtained images are provided to the controller 15.

As examples, the interventional tool 44 is a guide wire, a catheter, a stent placement tool or a balloon tool.

The display device 60 is any monitor, screen, or the like suitable for presenting a graphical user interface (GUI) capable of presenting live images in conjunction with a video playback loop as described herein. The display device 60 includes a plurality of screens or at least one split screen configured to display, alongside one another, live images, which show the interventional tool in situ but do not show vessels in the absence of a contrast puff, and the video playback loop of a previous contrast puff. Further, a previously acquired, i.e. not live, contrast enhanced angiogram is displayed, in accordance with various embodiments.

The electrocardiogram sensor 70 is any sensor configured to provide a cardiac signal indicating a length of time of each cardiac cycle, i.e. heartbeat, and to identify timing of phases of the cardiac cycle.

The controller 15 includes at least one processor 16 and a computer readable storage device, memory or media 18. The processor 16 can be any custom made or commercially available processor, a central processing unit (CPU), a graphics processing unit (GPU), an auxiliary processor among several processors associated with the controller 15, a semiconductor based microprocessor (in the form of a microchip or chip set), a macroprocessor, any combination thereof, or generally any device for executing instructions. The computer readable storage device, memory or media 18 may include volatile and nonvolatile storage in read-only memory (ROM), random-access memory (RAM), and keep-alive memory (KAM), for example. KAM is a persistent or non-volatile memory that may be used to store various operating variables while the processor 16 is powered down. The computer-readable storage device, memory or media 18 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 15 in controlling the imaging system 10. The instructions are configured for executing the modules of the controller 15 of FIG. 1, the data flow processes of FIG. 2 and the methods of FIG. 3 as described further herein.

The instructions may include one or more separate programs, each of which comprises an ordered listing of executable instructions for implementing logical functions. The instructions, when executed by the processor 16, receive and process images from the image acquisition machine 30, perform logic, calculations, methods and/or algorithms for automatically controlling modules of the image acquisition machine 10, and generate control signals to the display device 60 for displaying a video playback loop and live imaging as described herein. Although only one controller 15 is shown in FIG. 1, embodiments of the imaging system 10 can include any number of controllers 15 that communicate over any suitable communication medium or a combination of communication mediums and that cooperate to process images, perform logic, calculations, methods, and/or algorithms, and generate control signals to automatically control features of the imaging system 10.

The controller 15, such as a general-purpose computer, is operably connected to the image acquisition machine 30, controls operation of the image acquisition machine 30 for performing scans to obtain a stream of images and processes the images from the image acquisition machine 30. The processed images presented on the display device 60 of the imaging system 10.

The controller includes a number of modules 100 for executing the imaging systems and methods described herein to receive a stream of images, identify and extract contrast enhanced images from neighboring images in the received stream that have not been contrast enhanced and to generate a video playback loop of the extracted contrast enhanced images. The modules 100 described herein include at least one processor 16, a memory 18 and computer program instructions stored on the memory 18 for implementing the various functions and processes described with respect to the modules 100. Although separate modules 100 are described herein for particular functions, this does not exclude an integrated topology. Further, the shown modules 100 may be divided into further sub-modules. The modules 100 are in communication with one another as necessary to implement the features, processes and systems described herein.

The modules 100 will be described additionally with respect to the data flow diagram of FIG. 2 to illustrate exemplary functions and effects of each module 100.

Data receiver 14 is configured to receive a stream of images 102. The images 102 are X-ray images showing an interventional tool in situ within a vessel of the patient 36, in accordance with various embodiments. The images 102 are, for example, fluoroscopic images 102. Images are acquired by the image acquisition machine 30. Each image 36 represents a frame of image data that together, when displayed, constitute a video. A frame rate of images 102 is generally between 1 and 60 frames per second or more specifically between 15 and 30 frames per second. That is, images are acquired by the image acquisition machine 30 and received at the data receiver 14 at such frame rates. The data receiver 14 is configure to route the stream of images 102 to various other modules of the controller 15 including the display generator 50, the cardiac synchronizer and/or the contrast agent detector 20.

In embodiments, a contrast injection takes place such that certain images 102 will be contrast enhanced images 103. That is, a sequence of images 104 within the stream of images 102 will be contrast enhanced images 104. The transient nature of the contrast injection means that neighboring images 102 received before the contrast enhanced images 104 and neighboring images 102 received after the contrast enhanced images 104 are not contrast enhanced. However, a group of uninterrupted contrast enhanced images 104 are identifiable for the purpose of illuminating vessels. The contrast agent is, in various embodiments, injected through a catheter of the interventional tool 44 from which a balloon implement, a guide wire or other implement can movably extend. The contrast agent may, in some instances, be injected from the catheter without a further tool extending therefrom. The contrast agent is, in accordance with an exemplary embodiment, injected using a pump that is controlled by a gated contrast agent controller 64 for ensuring that the contrast agent injection lasts for at least one heartbeat.

Contrast agent detector 20 is configured to receive each image of the stream of images 102 and to automatically detect contrast enhanced images 104 within the images 102, or a defined portion thereof. The contrast agent detector 20 groups those images 104 that have been identified as including contrast agent and pass the contrast enhanced images 104 to the image extractor 22. Accordingly, contrast agent detector 20 is configured to identify image frames 104 that containing contrast agent, and to group them into a temporal cluster representing a contrast agent puff. The contrast agent detector 20 can be considered an image filter that allows contrast enhanced images 104 to pass and that removes images 102 that are not identified as being contrast enhanced.

There are various possibilities for automatically detecting contrast enhanced images 104. Generally, the contrast agent detector 20 is configured to use an image processing technique to identify contrast enhanced images 104. One possibility is to monitor image at least one parameter that either indicates presence of contrast agent in the image (such as a mean brightness of the image, or a surface of the image whose brightness is under a defined percentage, e.g. 20%, of a maximum brightness), or that indicates a visibility of vessels in the image (such as a mean ridgeness of the image, wherein ridgeness is a response to an elongated filter that enhances vessels). An increase of the at least one parameter, e.g. an increase beyond a predetermined threshold, is used to indicate that images meeting this requirement are contrast enhanced images 104. Another possibility is to use an image processing technique including detecting vessel segments in each frame of an image sequence and to determine a score vector for the fluoroscopic image sequence based on the detected vessel segments in each frame of the fluoroscopic image sequence. A contrast agent injection is determined to be present in the fluoroscopic image sequence based on the score vector. Further information on this possibility is found in US2012230558. Other possibilities include using deep-learning by training a neural network to identify contrast enhanced images 104 from non-contrast enhanced images.

Contrast agent detector 20 is configured for automatically detecting contrast agent on a global and/or a local basis. A global approach entails detecting presence of contrast agent throughout each image. A local approach entails detecting presence of contrast agent in a localized, e.g. limited, field of each image. In some embodiments, the controller 15 includes a localizer 62 configured to provide localization data 106 to the contrast agent detector 20. The localization data 106 is used by the contrast agent detector 20 to define the local field of each image. The localizer 62 is configured to receive the stream of images 102 and to analyze each image 102 to determine a location of interest. Based on the location of interest, position data 106 and optionally size data 106 are provided to the contrast agent detector 20 for use in defining the local field in each image. The localizer 62 is, in one example, configured to automatically detect the location of interest, e.g. through image processing. For example, the location of interest is detected based on at least one image feature. For example, the image feature is associated with the interventional tool 44 such as a distal end thereof. In one embodiment, the location of interest is identified automatically by segmenting the interventional tool 44 such as a guide wire or a balloon implement. The localizer 62 is configured to provide position data 106 corresponding to the location of interest. In exemplary embodiments, the localizer 62 is configured to further provide size or area data 106 corresponding to an area around the location of interest. The area around the location of interest is a boundary having a preset size and shape in some embodiments, centered to the location of interest.

The contrast agent detector 20 is configured to operate in either a local mode or a global mode or the contrast agent detector 20 is able to switch between local and global modes depending upon a setting, which may be user selectable. In the local mode, the contrast agent detector 20 is configured to restrict automatic detection to the local field as defined by the localization data 106 provided by the localizer 62. In this way, the contrast agent detector 20 is configured to select frames presenting contrast within the local field, which corresponds to the location of interest and the area around the location of interest defined according to the localization data 106. In the global mode, the contrast agent detector 20 is configured to detect the presence of contrast agent anywhere in the image. Image extractor 22 is configured to receive the contrast enhanced images 104 as identified and grouped by the contrast agent detector 22. Image extractor 22 is further configured to receive a cardiac signal 116 indicative of at least a length of a cardiac cycle, e.g. the heart rate. In embodiments, the cardiac signal 166 is able to designate at least one phase of the cardiac cycle. Image extractor 22 is configured to change a temporal length of the contrast enhanced images 104 to fit with one or an integer number of cardiac cycles to thereby output a set of contrast enhanced, cardiac cycle fitting images 108. For example, at least one frame is added or removed to the contrast enhanced images 104 by the image extractor 22. In various embodiments, at least one frame is added or removed from at least one end of the sequence of contrast enhanced images 104. In other embodiments, at least one frame is added or removed within the sequence of contrast enhanced images.

In another example, if the incoming set of contrast enhanced images 104 contains more than one heart cycle, the image extractor 22 discards less relevant frames. For instance, frames determined by the contrast agent detector to have less contrast agent therein, usually, at the extremities of the incoming set of contrast enhanced images 104, are discarded. Alternatively, a maximum for the at least one parameter is derived by the contrast agent detector and frames that are a threshold under the at least one parameter are liable for rejection. Irrespective of the particular trimming techniques used, the image extractor 22 is configured to discard frames until a length of the set of contrast enhanced images 104 equates to an integer number of cardiac cycles. In this way, the image extractor not only fits the contrast enhanced images 104 but also filters out less informative images having lower contrast agent therein than the kept images 108.

In another example, if the incoming set of contrast enhanced images 104 contains less than one heart cycle, the set of contrast enhanced images 104 is extended by including neighboring (non-injected) frames.

In embodiments, the display generator 50 is configured to receive the set of contrast enhanced, cardiac cycle fitting images or extracted images 108 and to generate a display including a video playback loop 120 of the extracted images 108. That is, the extracted images 108 are formed into a seamless loop so that at an end of the extracted images 108, the generated video returns to the beginning of the loop without interruption with respect to the frame rate of the extracted images 108. The display generator 50 is configured to run the video playback loop 120 continuously. The display generator 50 is configured to generate a display of a live video 122 of the stream of images 102 received by the data receiver 14 alongside, or otherwise in conjunction with, the video playback loop. The video 122 is considered to be live as it represents a most up to date picture of the interventional procedure. In general, the live video 122 is not contrast enhanced, except for any transient periods of contrast puff injection, and thus does not display vessels. Nonetheless, a fairly up to date picture of the vessels is able to be viewed through the video playback loop 120. The display generator 50 is, in some embodiments, further configured to display a still image, which can be a three-dimensional representation, of vessels obtained by the image acquisition machine 30, or another image acquisition machine, previously such as during a diagnosis or preparation phase. The still image is displayed alongside or otherwise in conjunction with the live video 120 and optionally also the video playback loop 120. The live video 122, e.g. a live fluoroscopic video, the video playback loop 120 and optionally the still image together make up a generated display 110.

The display generator 50 is configured to provide the generated display 50 to the display device 60 for presentation to the clinician.

In some embodiments, the video playback loop 120 is synchronized, with respect to cardiac phases, to the live video 122 by a cardiac synchronizer 24. The cardiac synchronizer 24 is configured to receive at least one frame of the extracted images 108 and a cardiac signal 116 associated therewith, and to receive at least one most recent frame 114 of the stream of images 102 and a cardiac signal 116 associated therewith. The cardiac synchronizer 24 is configured to align, with respect to cardiac phase, the extracted images 108 and the stream of fluoroscopic images 102 based on the cardiac signals 116. The cardiac synchronizer 24 is configured to output a frame 112 of the extracted images 108 and a most recent frame 114 of the stream of images 102 that are cardiac synchronized to one another. Alternatively, the cardiac synchronizer 24 outputs data 112 coordinating cardiac synchronization. The display generator 50 is configured to use cardiac synchronization data 112 provided by the cardiac synchronizer, which may be in the form of cardiac synchronized frames of extracted images 108 and live images 102, to generate a display 110 including the live video 122 and the video playback loop 120 that are cardiac synchronized to one another. In this way, a clinician is able to use a display of the video 120 as a vascular roadmap through synchronous display with the live video 122 of fluoroscopic images. In other words, contrast enhanced images 120 are displayed at the same heart phase as the live images 122.

The cardiac signal 116 used by the image extractor 22 and the cardiac synchronizer 24 is provided by the cardiac signal generator 26. The cardiac signal generator 26 is configured to generate the cardiac signal 116 based on signals received from the ECG sensor 70 identifying cardiac cycle and phase information or by analyzing images 102 to determine cardiac cycle and phase information. Under the image processing alternative, the cardiac signal generator 26 is configured to extract a periodic signal from analysis of the images 102 that will allow temporal synchronization of both the live images 102 and the sequence of extracted images 108. The periodic signal is extracted, in some embodiments, through variation of contrast in a given region or periodic motion of a segmented tool 44.

In some embodiments, a cardiac signal 116 is not necessary. For example, the cardiac synchronizer 24 is configured to correlate the live fluoroscopic image 102/104 with the extracted images 108. One possibility would be to perform such correlation using catheter shape matching between live and injected images 102, 108 to perform cardiac synchronization.

Figure 2:
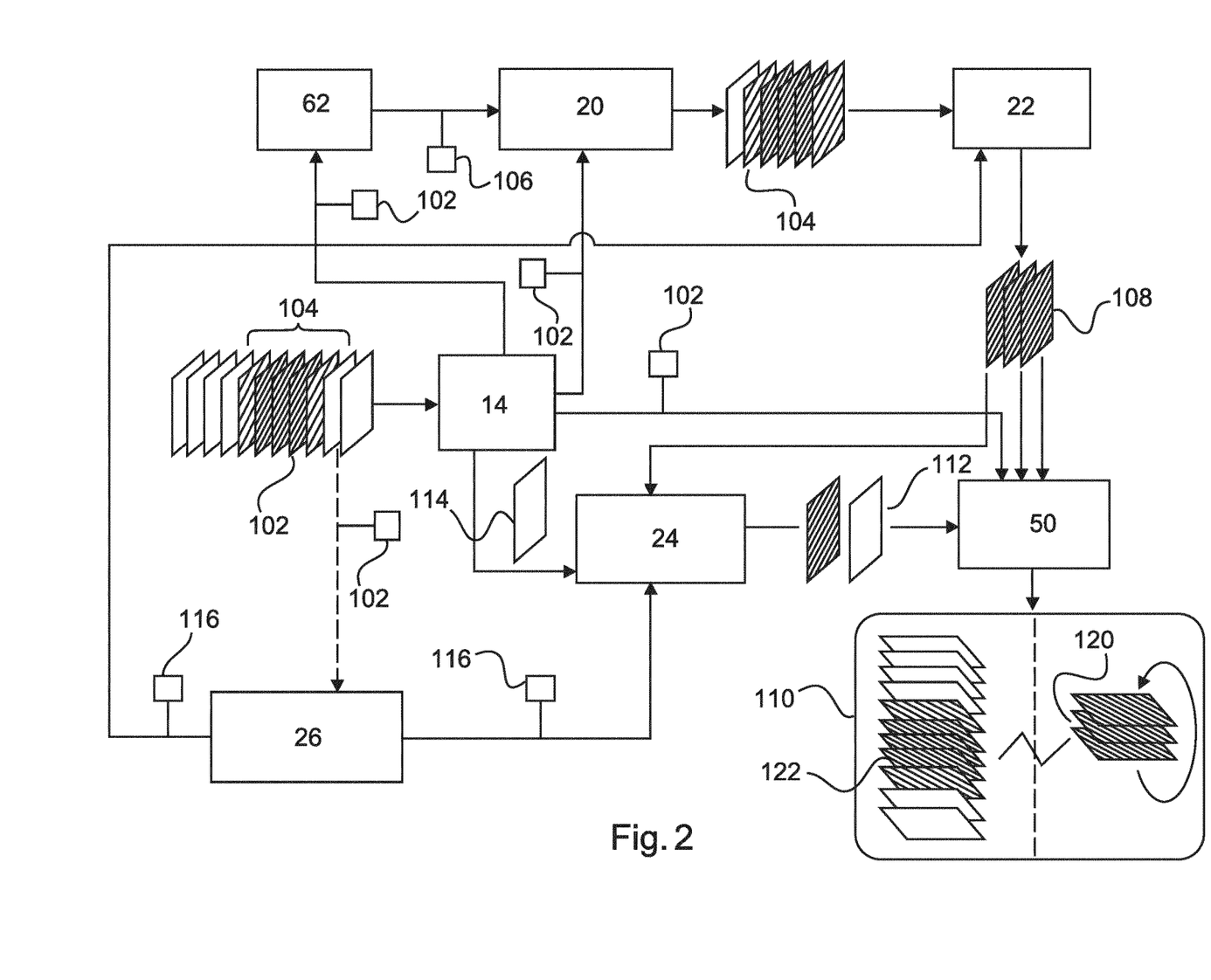
FIG. 2 is a data flow diagram illustrating flow of data between various modules of the controller of FIG. 1, in accordance with various embodiments.
Figure 3:
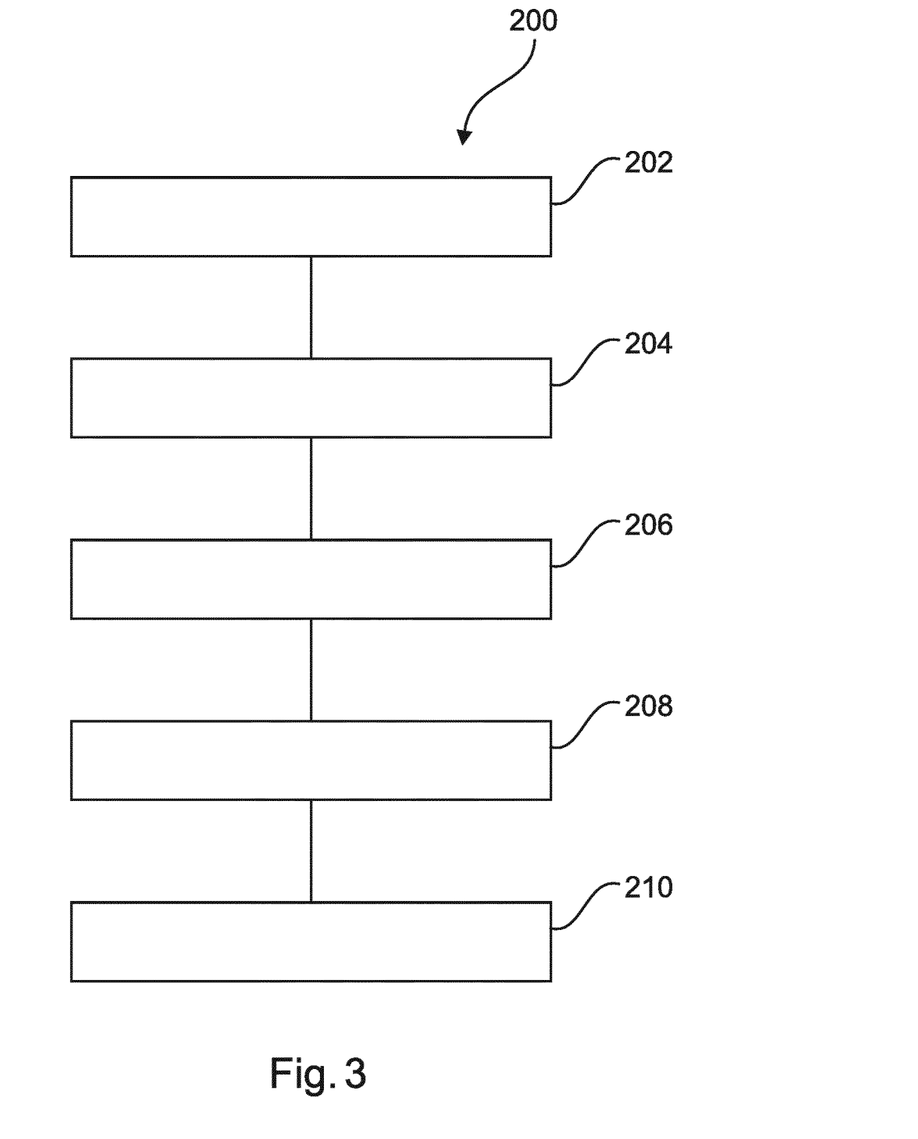
FIG. 3 is a flow chart illustrating a computer implemented method for imaging, in accordance with various embodiments.

Referring now to FIG. 3, and with continued reference to FIGS. 1 and 2, a flowchart illustrates a computer implemented imaging method 200 that can be performed by the imaging system 10 of FIG. 1 in accordance with the present disclosure. As can be appreciated in light of the disclosure, the order of operation within the method is not limited to the sequential execution as illustrated in FIG. 3, but may be performed in one or more varying orders as applicable and in accordance with the present disclosure. In various embodiments, the method 200 can be scheduled to run based on one or more predetermined events, and/or can run continuously during operation of the imaging system 10.

The computer implemented method 200 includes a step 202 of receiving a stream of images 102. Step 202 is executed through the data receiver 14. The images 102 have been obtained by the image acquisition machine 30 and are generally X-ray images 102, particularly fluoroscopic images 102. The stream of images 102 usually include images of the interventional tool 44 located intravascularly within the patient 36. At some point during live display based on the stream of images 102, a puff contrast injection may be required in order to enable visualization of vessel structure, such as when the tool 44 approaches a stenosis. The contrast injection is optionally performed through a gated contrast injector that is controlled to ensure the inject lasts at least one cardiac cycle. The contrast injection will result in some of the stream of images 102, for a brief period of time (e.g. about 0.5 to about 1.5 seconds) being contrast enhanced images 104.

The computer implemented method 200 includes a step 204 of automatically identifying the contrast enhanced images 104. Step 204 is generally executed through the contrast agent detector. The contrast enhanced images 104 are automatically identified using an image processing technique, as described herein. A global or local field of detection is used in alternative embodiments, as described herein. Step 204 results in a selection of a group of contrast enhanced images 104.

The computer implemented method 200 includes a step 206 of extracting contrast enhanced, cardiac cycle fitting images 108. Step 206 is executed through the image extractor 22. Step 206 temporally extends or shortens the group of contrast enhanced images 104 from step 204 to fit with one cardiac cycle or a plural integer number of heart cycles. In the case of shortening the time span of the group of contrast enhanced images 104, frames are removed from the start and end of the sequence that are determined to have lower amounts of contrast agent therein than frames that are kept, in accordance with various embodiments. The process of cardiac cycle fitting makes use of the cardiac signal 116 including information on the temporal length of the cardiac cycle.

The computer implemented method 200 includes a step 208 of cardiac synchronizing the extracted images 108 from step 206 and live images 102 with respect to cardiac phase so that a display of the extracted images 108 and the live images 102 are aligned with respect to cardiac phase. The cardiac synchronization step 208 uses the cardiac signal 116 including cardiac phase information to produce cardiac synchronized extracted and live images 112.

The computer implemented method 200 includes a step 210 of displaying a video playback loop 120 of the extracted images 108 and a live video 122 of the stream of images 102 that are cardiac synchronized with one another. Step 210 is executed through the display generator. The video play back loop 120 and the live video 122 are played alongside one another, e.g. on either side of a split screen boundary or in neighboring screens.

The methods and systems disclosed herein propose to detect contrast enhanced frames 104, extract those frames 104 and replay the contrast enhanced frames 104 in a loop in a sequence alongside live images 102, e.g. fluoroscopic images. In this way, a clinician is able to analyze vasculature details more in depth than with a transient live puff. Further, the looped video 120 of the relevant cycles of the puff, played synchronously or otherwise in conjunction with the live fluoroscopy video 122, serves as an up-to-date local roadmap for next steps of an interventional procedure. The looped injected sequence 120 can show other regions of the vasculature that can be valuable later in the intervention. The systems and methods described herein are generally applicable to percutaneous interventional procedures that use live imaging to guide movement of an interventional tool 44.

In another exemplary embodiment of the present invention, a computer program or a computer program element is provided that is characterized by being adapted to execute the method steps of the method according to one of the preceding embodiments, on an appropriate processing system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system for an imaging assisted interventional procedure, comprising:
   at least one processor configured to:
      receive a stream of images of a region of interest, wherein the stream of images comprises a sequence of live images of the region of interest being captured during an interventional procedure, identify, in the stream of images, a sequence of contrast-enhanced images that have been contrast enhanced through an injection of a puff of contrast agent, extract the sequence of contrast-enhanced images from the stream of images, generate a playback loop of only the sequence of contrast-enhanced images, and display the sequence of live images being captured during the interventional procedure in a first display area and repeatedly replay the playback loop of only the sequence of contrast-enhanced images, synchronized to the displayed sequence of live images, in a second display area.

2. The imaging system of claim 1, wherein the at least one processor is further configured to automatically detect the sequence of contrast-enhanced images in the stream of images by application of an image processing technique that filters contrast enhanced images from images that have not been contrast enhanced.

3. The imaging system of claim 1, wherein the at least one processor is further configured to change a temporal length of the sequence of contrast-enhanced images for cardiac synchronization.

4. The imaging system of claim 3, wherein the at least one processor is further configured to trim or extend the sequence of contrast-enhanced images to temporally fit within one cardiac cycle or an integer number of cardiac cycles.

5. The imaging system of claim 1, wherein the at least one processor is further configured to temporally synchronize the sequence of contrast-enhanced images and the sequence of live images with respect to cardiac phases.

6. The imaging system of claim 5, wherein the at least one processor is further configured to generate the display of the sequence of live images and the repeatedly replayed playback loop of the sequence of contrast-enhanced images temporally synchronized to one another with respect to cardiac phases.

7. The imaging system of claim 3, wherein the at least one processor is further configured to output a cardiac signal for use in the cardiac synchronization, wherein the cardiac signal is indicative of a cardiac cycle.

8. The imaging system of claim 7, further comprising at least one of an electrocardiogram sensor and wherein the at least one processor is further configured to execute an image processing technique configured to derive the cardiac signal from the stream of images.

9. The imaging system of claim 1, wherein the at least one processor is further configured to identify images that have been contrast enhanced in a localized area of a global field of view of the stream of images and to extract a sequence of the identified contrast-enhanced images having the contrast enhanced localized area from the stream of images.

10. The imaging system of claim 9, wherein the at least one processor is configured to determine the localized area based on identification of an object of interest through an image processing technique.

11. The imaging system of claim 1, wherein the at least one processor is further configured to generate a contrast injection control configured to cause an interventional device to contrast enhance a set of images that is at least one heart cycle in length.

12. The imaging system of claim 1, further comprising:
an image acquisition machine configured to generate the stream of images of the region of interest;

a display device configured to display the sequence of live images from the stream of images in the first display area and to repeatedly replay the playback loop of only the sequence of contrast-enhanced images in the second display area;

an interventional tool configured to inject the puff of contrast agent into the region of interest to produce the contrast-enhanced images in the stream of images of the region of interest, the interventional tool configured to inject the contrast agent for an injection period of less than one second; and an electrocardiogram sensor configured to measure a cardiac signal indicating a length of time of a cardiac cycle.

13. The imaging system of claim 1, wherein the at least one processor is further configured to:
inject the contrast agent for an injection period of less than one second to produce the contrast-enhanced images in the stream of images of the region of interest.

14. The imaging system of claim 1, wherein, to identify the sequence of contrast-enhanced images, the at least one processor is further configured to be switched between (a) a global mode in which the at least one processor is configured to identify a contrast-enhanced image by checking for a presence of contrast agent throughout the image, and (b) a local model in which the at least one processor is configured to identify a contrast-enhanced image by checking for a presence of contrast agent only within a defined location of interest in the image.

15. A computer implemented method for imaging assisted interventional procedure, the method comprising:
receiving a stream of images of a region of interest, wherein the stream of images comprises a sequence of live images of the region of interest being captured during an interventional procedure;

identifying, in the stream of images, a sequence of contrast-enhanced images that have been contrast enhanced through an injection of a puff of contrast agent;

extracting the sequence of contrast-enhanced images from the stream of images;

generating a playback loop of only the sequence of contrast-enhanced images; and displaying the sequence of live images being captured during the interventional procedure in a first screen area and the playback loop of only the sequence of contrast-enhanced images, synchronized to the displayed sequence of live images, in a second screen area.

16. The computer implemented method of claim 15, further comprising:
trimming or extending the sequence of contrast-enhanced images to temporally fit within one cardiac cycle or an integer number of cardiac cycles.

17. A non-transitory computer-readable storage medium having stored a computer program comprising instructions, the instruction, when executed by a processor, cause the processor to:
receive a stream of images of a region of interest, wherein the stream of images comprises a sequence of live images of the region of interest being captured during an interventional procedure;

identify, in the stream of images, a sequence of contrast-enhanced images that have been contrast enhanced through an injection of a puff of contrast agent;

extract the sequence of contrast-enhanced images from the stream of images;

generate a playback loop of only the sequence of contrast-enhanced images; and display the sequence of live images being captured during the interventional procedure in a first screen area and repeatedly replay the playback loop of only the sequence of contrast-enhanced images, synchronized to the displayed sequence of live images, in a second screen area.

18. The method of claim 15, further comprising:

injecting the contrast agent for an injection period of less than one second to produce the contrast-enhanced images in the stream of images of the region of interest.

19. The non-transitory computer-readable storage medium of claim 17, wherein, the instruction, when executed by a processor, further cause the processor to:

inject the contrast agent for an injection period of less than one second to produce the contrast-enhanced images in the stream of images of the region of interest.

\* \* \* \* \*